United States Patent [19]
Kosaka et al.

[11] Patent Number: 5,824,269
[45] Date of Patent: Oct. 20, 1998

[54] FLOW CYTOMETER

[75] Inventors: Tokihiro Kosaka; Hiroyuki Nakamoto; Fumio Kubota, all of Hyogo, Japan

[73] Assignee: Toa Medical Electronics Co., Ltd., Hyogo, Japan

[21] Appl. No.: 577,241

[22] Filed: Dec. 22, 1995

[30]     Foreign Application Priority Data

Dec. 26, 1994  [JP]  Japan .................................. 6-323134
Dec. 26, 1994  [JP]  Japan .................................. 6-323135

[51] Int. Cl.$^6$ .................................................. G01N 33/00
[52] U.S. Cl. ........................... 422/73; 422/82.05; 436/63;
              364/555; 250/461.2; 356/73; 356/337; 356/338
[58] Field of Search ........................... 422/73, 81, 82.05;
              436/52, 63; 250/461.2; 382/133, 134; 356/39,
              73, 317, 318, 337, 338; 364/555

[56]            References Cited

U.S. PATENT DOCUMENTS

| | | | |
|---|---|---|---|
| 5,159,397 | 10/1992 | Kosaka et al. | 356/73 |
| 5,247,340 | 9/1993 | Ogino | 356/73 |
| 5,325,169 | 6/1994 | Nakamoto et al. | 356/73 |
| 5,469,251 | 11/1995 | Kosaka et al. | 356/73 |
| 5,469,375 | 11/1995 | Kosaka | 364/555 |
| 5,471,294 | 11/1995 | Ogino | 356/73 |
| 5,521,699 | 5/1996 | Kosaka et al. | 356/73 |
| 5,548,395 | 8/1996 | Kosaka | 356/73 |

FOREIGN PATENT DOCUMENTS 63-394156   4/1988   Japan .

*Primary Examiner*—Maureen M. Wallenhorst

[57]            ABSTRACT

A flowcytometer includes a sheath flow cell for forming a sample stream containing particles; a detector for detecting the particle at a first area to generate a signal representative of the particle; an imaging device for capturing an image of the particle at a second area of the sample stream; a display; a calculator for calculating a plurality of characteristic parameters of each particle; a distribution preparation device for preparing a distribution of the characteristic parameters to display the distribution on the display; a designation device for previously designating a region in the distribution; a region memory for storing the designated region; a decision device for deciding whether the characteristic parameters of the particle detected at the first area by the detection means are located in the designated region stored in the region memory; an image controller for allowing the imaging device to imaging the particle when the characteristic parameters are located in the designated region; an image memory for storing the image of the particle; and a controller for selectively reading the image of the particle to allow the display device to display the read image.

11 Claims, 18 Drawing Sheets

FIG. 6
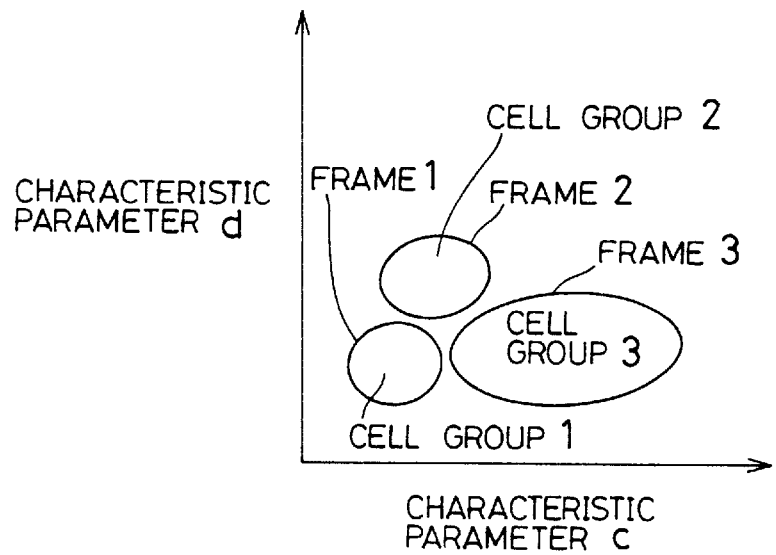
FIG. 7
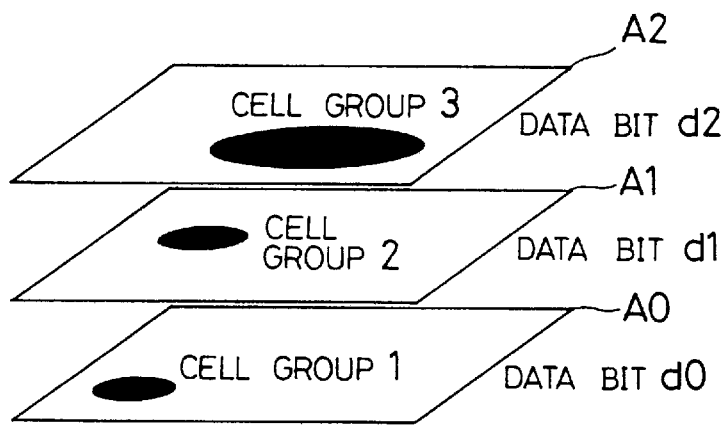
Regions (addresses) shown by ● are allowed to assume the data bit of '1' whereas the other regions (addresses) are allowed to assume the data bit of '0'

FIG. 16
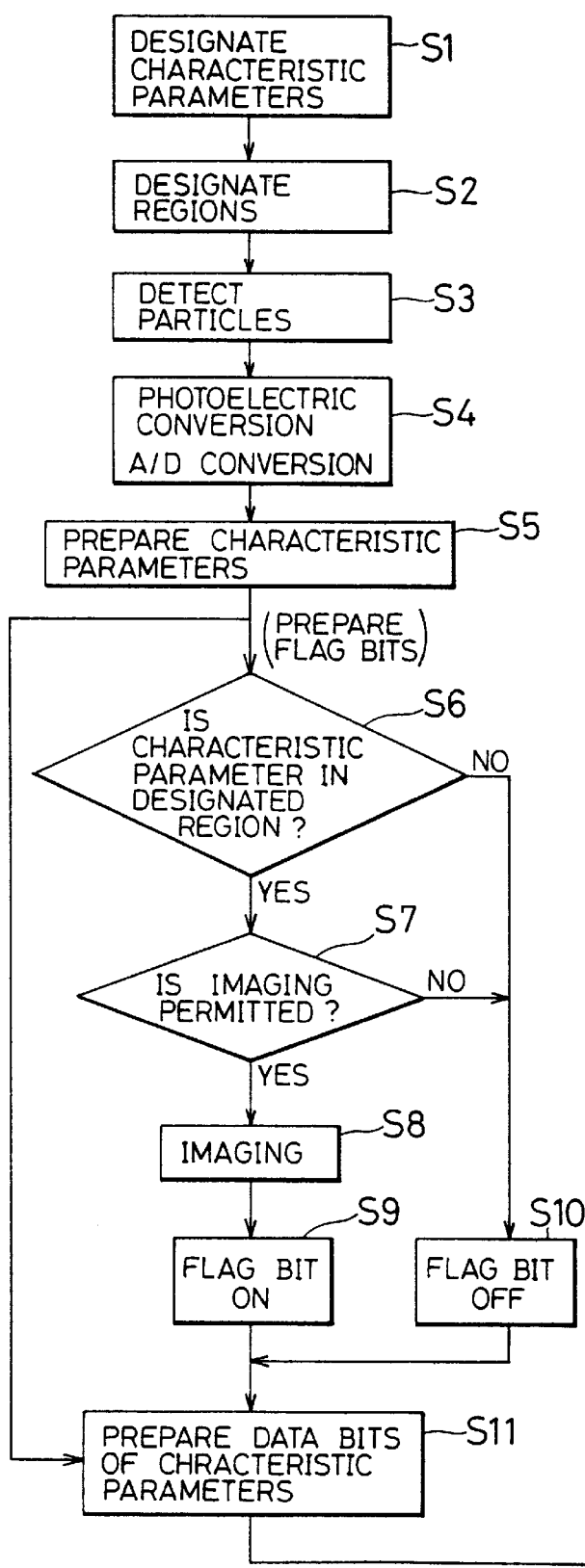
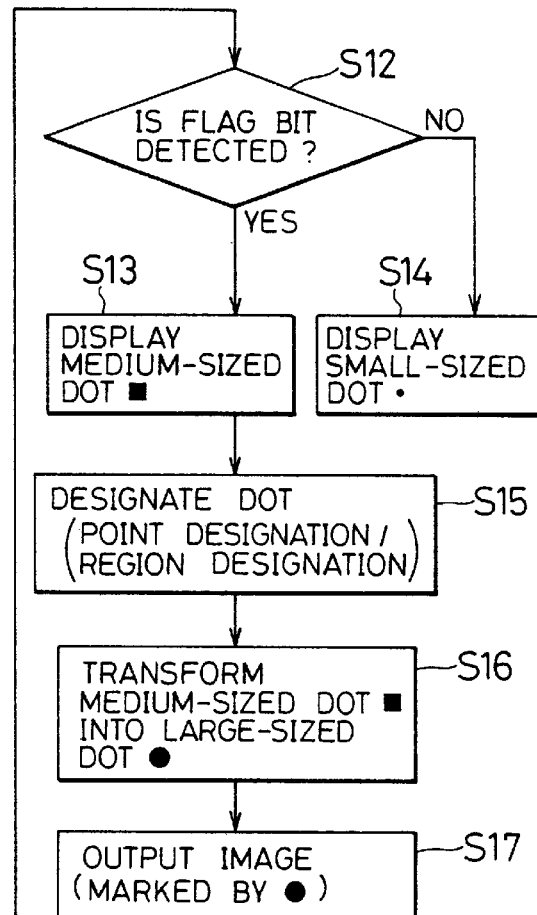

FIG. 20

| PARTICLE No. | CHARACTERISTIC PARAMETER | | | | FLAG |
|---|---|---|---|---|---|
| | a | b | c | d | |
| P1 | a1 (8 BITS) | b1 (8 BITS) | c1 (8 BITS) | d1 (8 BITS) | 1 |
| P2 | a2 | b2 | c2 | d2 | 0 |
| P3 | a3 | b3 | c3 | d3 | 1 |
| P4 | a4 | b4 | c4 | d4 | 0 |
| ... | ... | ... | ... | ... | ... |
| Pn | an | bn | cn | dn | 1 |

FLOW CYTOMETER

BACKGROUND OF THE INVENTION

1. Field of the Invention

The present invention relates to flow cytometers having a function of imaging a cell or particle flowing through a sheath flow cell.

2. Description of Related Art

There have been known flow cytometers which can image a cell of a desired size by introducing a cell suspended solution which is treated with a reagent such as a fluorescent dye into a narrow glass tube and applying a laser beam to a sample stream of the cell suspended solution flowing through the tube (see, for example, Japanese Unexamined Patent Publication No. SHO 63(1988)-94156).

Such flow cytometers, however, have constituted problems in that it is not easy to particularly designate the kind of cell or particle to be imaged and in that it is also not easy to select and display a desired image from a number of stored images.

SUMMARY OF THE INVENTION

An object of the present invention is to solve the aforementioned problems.

To fulfill the aforementioned and other objects, the present invention provides a flow cytometer comprising: a sheath flow cell for forming a sample stream containing particles; detection means for detecting the particle at a first area of the sample stream to generate a signal representative of the particle; imaging means for imaging the particle at a second area of the sample stream; display means; calculation means for calculating a plurality of characteristic parameters indicating characteristics of each particle based on the generated signal; distribution preparation means for preparing a distribution of the characteristic parameters and displaying the distribution on the display means; region designation means for previously designating at least one region in the distribution; region storage means for storing the designated region; decision means for deciding whether the characteristic parameters of the particle detected at the first area by the detection means are located in the designated region stored in the region storage means; imaging control means for allowing the imaging means to image the particle when the characteristic parameters are located in the designated region; image storage means for storing the image of the particle obtained by the imaging means; and displaying control means for selectively reading the image of the particle to allow the display means to display the read image.

An object of the present invention is to solve the aforementioned problems.

BRIEF DESCRIPTION OF THE DRAWINGS

FIG. 6 is an explanatory view for another example of the scattergram shown in FIG. 4 in accordance with the present invention;

FIG. 7 is an explanatory view for a bit map corresponding to the scattergram shown in FIG. 6 which is registered in the memory for registering distribution regions in accordance with the present invention;

FIG. 16 is a flowchart illustrating an operation in the second embodiment in accordance with the present invention;

FIG. 20 is an explanatory view for a data set of characteristic parameters in the second embodiment in accordance with the present invention.

DESCRIPTION OF THE PREFERRED EMBODIMENTS

Figure 1:
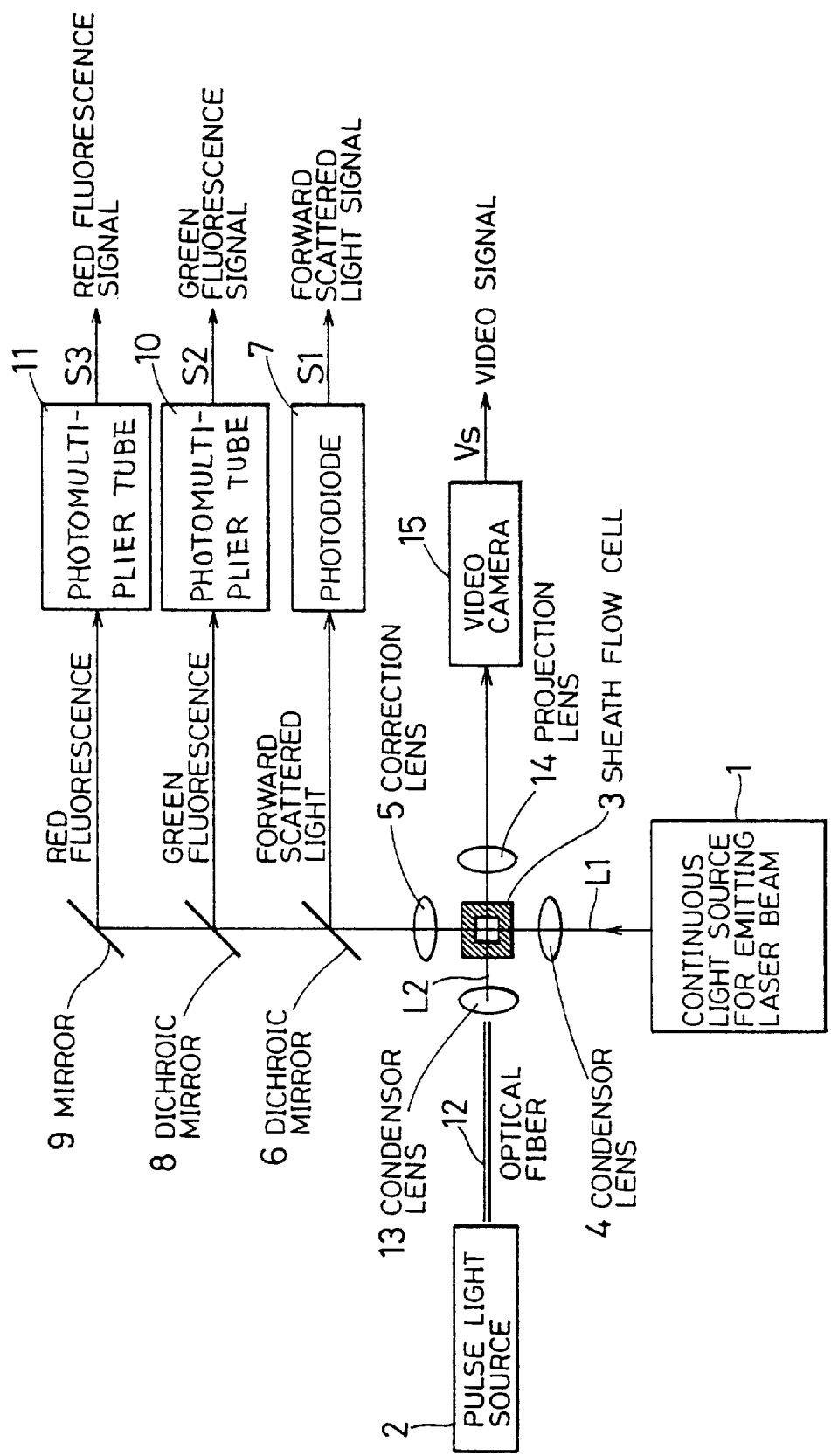
FIG. 1 is an explanatory view for the construction of an optical system in a first and second embodiments in accordance with the present invention.

The present invention will hereinafter be described in detail by way of embodiments thereof shown in the attached drawings. These embodiments are not intended to limit the scope of the present invention.

The sheath flow cell of the present invention is a flow cell that allows a sample liquid containing particles which is enclosed by a sheath liquid to flow therethrough to form a narrow stream of the sample liquid due to a hydrodynamic effect. The sheath flow cell can be of a conventional type.

Particles to be measured by the flow cytometer of the present invention are mainly blood cells contained in blood or urine, but the particles may be microbes such as yeasts or lactic acid bacteria, or particles for industrial use. In order to classify the kind of a blood cell or cell, a nucleic acid, for example, may be reacted with a specific fluorescent reagent, and the fluorescence intensity thereof can be measured.

Detection methods for detecting a particle include electrical and optical detection methods, which utilize, for example, a first light source for applying light to the first area of the sample stream (for example, a continuous light source for continuously emitting light, such as a laser, or a halogen lamp or a tungsten lamp) and an optical detection device for optically detecting a particle illuminated by the first light source and outputting the intensity of light such as scattered light and fluorescence of the particle (for example, a photodiode, a phototransistor or a photomultiplier tube).

To capture images, it is preferred to provide a light source for applying light to the second area of the sample stream. The light source may be either a continuous or intermittent light source. The continuous light source can be one that continuously emits light such as a laser, a halogen lamp or a tungsten lamp, while the intermittent light source can be one that intermittently emits light such as a pulse laser (for example, 7000 series manufactured by Spectra-Physics Co., Ltd.) or a multi-stroboscope (for example, DSX series manufactured by Sugawara Laboratories, Inc., Japan). In general, it is preferred that the continuous light source is used as an intermittent light source by being combined with an optical shutter, such as a unit utilizing a known acousto-optic modulator or electro-optic modulator.

As an imaging device for imaging the particle, an ordinary camera or still camera for imaging a two-dimensional image may be used. However, depending on applications, it is preferred to use a camera provided with an image intensifier for intensifying weak light that may further include a shutter (gate). The second area may be located either downstream from the first area or at a place similar to that of the first area.

The display of the present invention, which may also serve as a printer, may be a CRT, a liquid crystal display or a printer.

The calculation device for calculating a plurality of characteristic parameters indicating characteristics of each particle based on the generated signal; distribution preparation device for preparing a distribution of the characteristic parameters and displaying the distribution on the display; region storage device for storing a region designated in the distribution; decision device for deciding whether the detected characteristic parameters are located inside the designated region stored in the region storage device; imaging controller for allowing the imaging device to image the particle; image storage device for storing the image of the particle obtained by the imaging means; and displaying controller for selectively reading the image of the particle to allow the display to display the read image, utilize a microcomputer comprising a signal processing circuit, a CPU, a ROM and a RAM.

By distribution it means anything that shows the distribution state of characteristic parameters, and a preferred example of distribution is a two-dimensional scattergram. Preferably, an input device such as a key board or a mouse is used as parameter designation device for previously designating at least one pair of characteristic parameters among the plurality of characteristic parameters; and region designation device for previously designating at least one region in each displayed distribution.

In the present invention, a plurality of distributions may be designated and displayed so that the distribution preparation device prepares a plurality of distributions based on the characateristic parameters designated by the parameter designation device and displays the plurality of distributions on the display and the imaging device images the particle when the plurality of characteristic parameters for the particle detected by the detection device are located in the designated regions of the plurality of distributions.

The region designation device may designate a plurality of regions in a distribution. The imaging device may image the particle when the plurality of characteristic parameters for the particle detected by the detection device are located in any one of the designated regions of the plurality of distributions.

The region storage device stores the designated region by allowing memory addresses thereof to correspond to the characteristic parameters so that data bits inside the designated region and data bits outside the designated region are represented by different binary data. The decision device may decide whether the characteristic parameters are located in the designated region based on the binary data.

The present invention may further include device for presetting the number for imaging times of the imaging device, with respect to each region designated by the region designation device.

The imaging controller may comprise a triggering signal generating device for generating a signal every time the particle reaches the second area based on the generated signal to trigger the imaging device.

Moreover, the present invention may further include a coordinate designation device for designating a coordinate point in the distribution, wherein the displaying controller, when the coordinate designation device designates a coordinate point corresponding to the imaged particle, reads the image of the particle corresponding to the designated coordinate point to allow the display to display the read image.

As mentioned above, the present invention identifies the kind of a cell in real time by using a plurality of characteristic parameters obtained by the detection system, images the predetermined number of cells of a desired kind or cells of a kind unable to be classified, and flexibly sets imaging conditions on how many cells of what kinds are imaged or the like.

The present invention will hereinafter be described in detail by way of embodiments thereof shown in the attached drawings. These embodiments are not intended to limit the present invention.

EMBODIMENT 1

Figure 2:
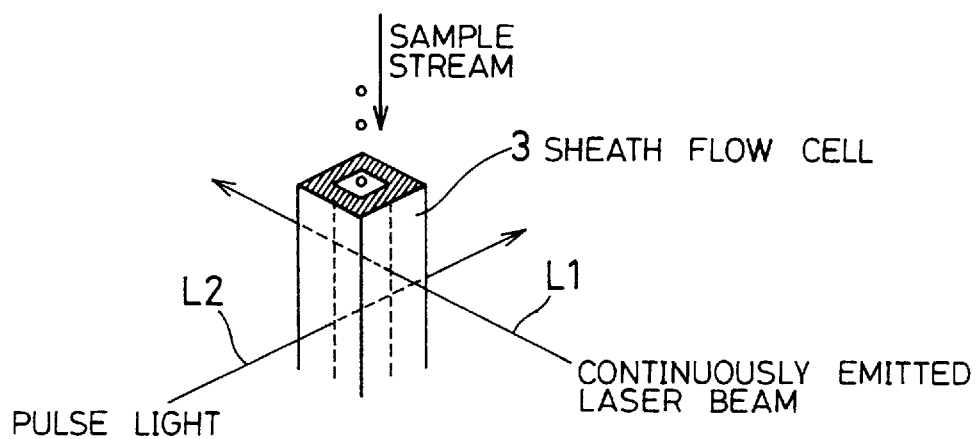
FIG. 2 is a perspective view illustrating an essential part in the optical system of FIG. 1 in accordance with the present invention.

FIGS. 1 and 2 illustrate an optical system in a first embodiment of the present invention, where two light sources are employed: a continuous light source 1 for emitting laser beam to detect scattered light or fluorescence and a pulse light source 2 for capturing images of cells. Light beams L1 and L2 respectively from the light sources 1 and 2, as shown in FIG. 2, are directed to intersect each other at right angles orthogonally with respect to a rectangular sheath flow cell 3 (the direction of a sample stream in FIG. 1 is perpendicular to a paper surface of the drawing). In addition, pulse light for capturing images of cells is directed to the sample stream through the sheath flow cell 3 downstream (for example, about 0.5 mm) from an irradiation site given by the continuous light source 1 for emitting a laser beam. Such positional shifting of the irradiation sites enables the formation of clear images of cells which are not affected by scattered light or fluorescence from the cells, or continuous light from the light source for emitting the laser beam.

A cell suspended solution treated with an appropriate reagent is introduced to the sheath flow cell 3 to form a sample stream which is narrowed by being enclosed in a sheath liquid. Continuously emitted laser beam is finely focused by a condenser lens 4 to be directed to the sample stream. Scattered light or fluorescence emitted by cells which are passing at the irradiation region is condensed by a collector lens 5. Then, the scattered light is reflected by a dichroic mirror 6 to be received by a photodiode 7. the green and red fluorescences are reflected by dichroic mirrors 8 and 9 and are received and intensified by photomultiplier tubes 10 and 11, respectively.

Figure 3:
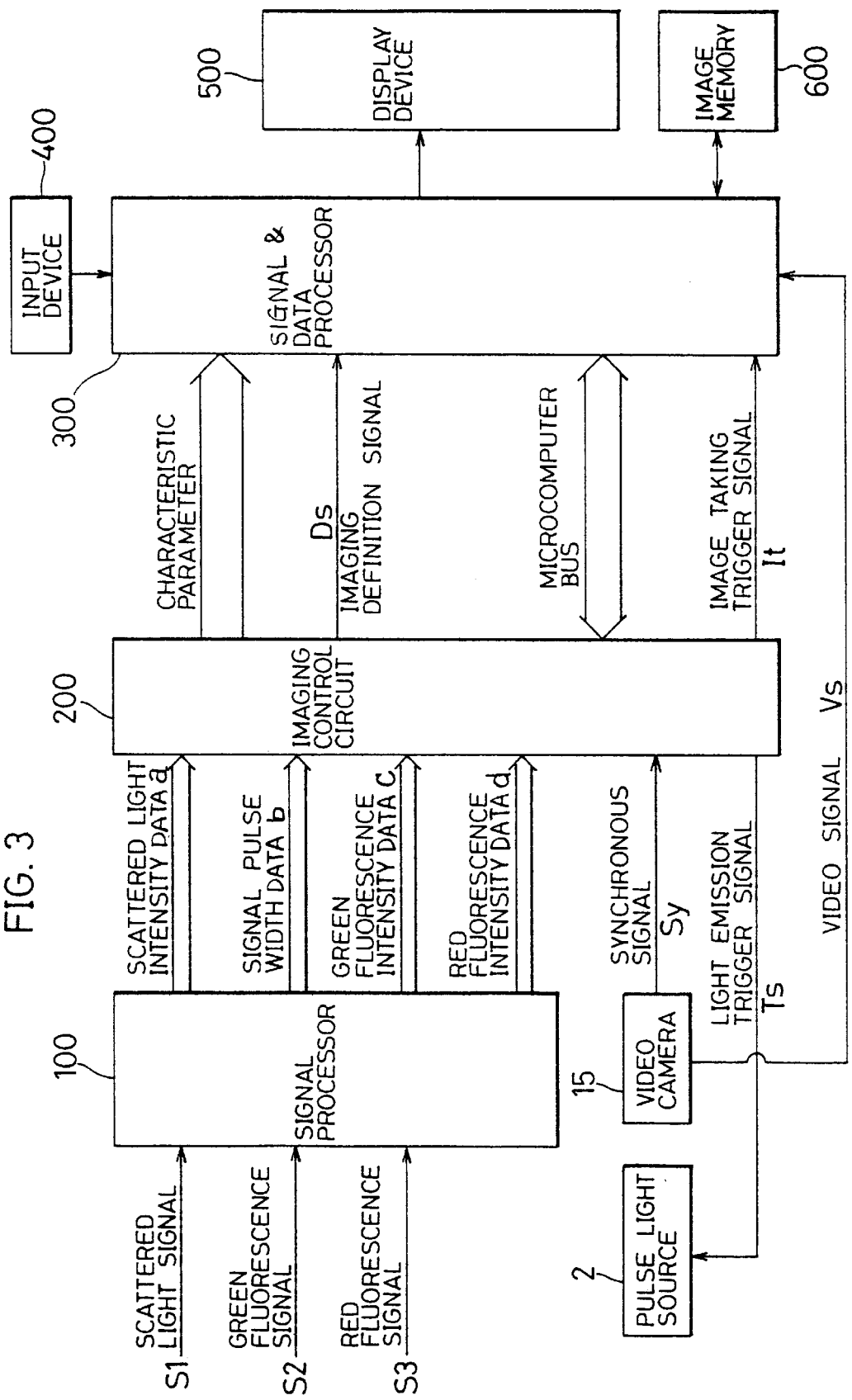
FIG. 3 is a block diagram illustrating a signal processing system in the first embodiment in accordance with the present invention.

A scattered light intensity signal S1 and fluorescent light intensity signals S2 and S3 detected by the photodiode 7 and the photomultiplier tubes 10 and 11 are sent to a signal processor 100 as shown in FIG. 3 to output information on height, area, width or the like of each pulse of the detected signals, as A/D converted data.

FIG. 3 illustrates the construction of the signal processing system of the present embodiment in which the signal processor 100 provides four characteristic parameters comprising scattered light intensity a, signal pulse width b, green fluorescence intensity c and red fluorescence intensity d. An imaging control circuit 200 identifies each kind of cell in real time by using those parameters for control, such that cells of a kind designated to be imaged are selectively imaged. In particular, the imaging control circuit 200 compares the characteristic parameters of cells with the characteristic parameters of cells of a targeted kind and supplies, if it is determined that they are the cells to be imaged, light emitting trigger signals Ts for imaging the cells to the pulse light source 2.

The pulse light source 2 is a light source of the type that emits light merely momentarily (for about several nanoseconds) by the light emitting trigger signals Ts, so as to image flowing particles without image blur even at high sample stream velocity of several meters per second. Pulse light, as shown in FIG. 1, is introduced to the flow cell 3 by an optical fiber 12 and is narrowed by a condenser lens 13 to be directed to the sample stream. The irradiation through the optical fiber 12 reduces coherency of the pulse light, making it possible to capture images of cells with less diffraction fringes. The pulse light transmitted through the sample stream is focused on the photosensing surface of a video camera 15 via a projection lens 14, thereby capturing images of cells formed by the transmitted light. A video signal Vs from the video camera 15 is sent to a data processor 300 as shown in FIG. 3 to be stored and accommodated as a digital image in an image memory 600.

The characteristic parameters a to d for scattered light intensity, fluorescent light intensity or the like are sent to a data processor 300 so as to enable analysis and display for a scattergram (two-dimentional frequency distribution) prepared in combination of those parameters. An input unit 400 including a keyboard and a mouse designates a pair of characteristic parameters for preparing the scattergram, designates regions in the scattergram, and sets the numbers of image capturing and displaying conditions. Reference numeral 500 represents a display device for displaying scattergrams or images of particles.

In accordance with the present invention, factors such as the kind of a cell to be imaged can be preset in the scattergram displayed by the display device 500. An example thereof will now be described with reference to FIG. 4 in which the characteristic parameters a and b are plotted on two axes as the abscissa and ordinate, respectively. It is assumed that the distributions of cell groups A, B and C are previously acknowledged to be located in regions defined by frames 1, 2 and 3. The cell group B for example, when selected to be imaged, requires being encircled with the frame 2 by using the input unit 400. The imaging control circuit 200 determines whether values of the characteristic parameters a and b of each cell obtained by the signal processor 100 are located inside the region defined by the frame 2 in the scattergram of FIG. 4 and allows, if the values of the characteristic parameters are inside the region, the pulse light source 2 to emit light to image the cells.

Figure 5:
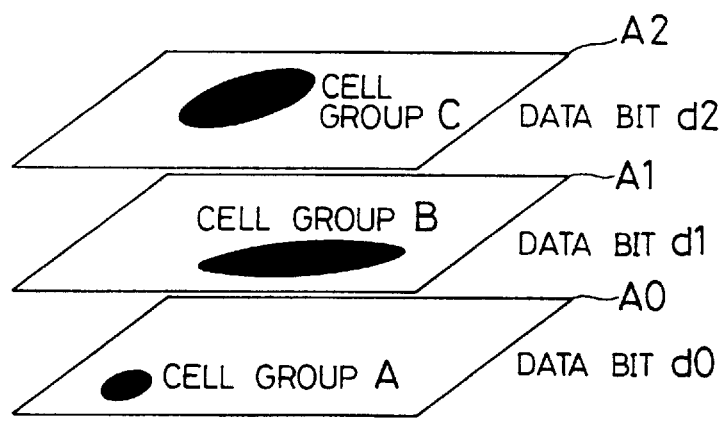
FIG. 5 is an explanatory view for a bit map corresponding to the scattergram shown in FIG. 4 which is registered in a memory for registering distribution regions in accordance with the present invention.
Figure 8:
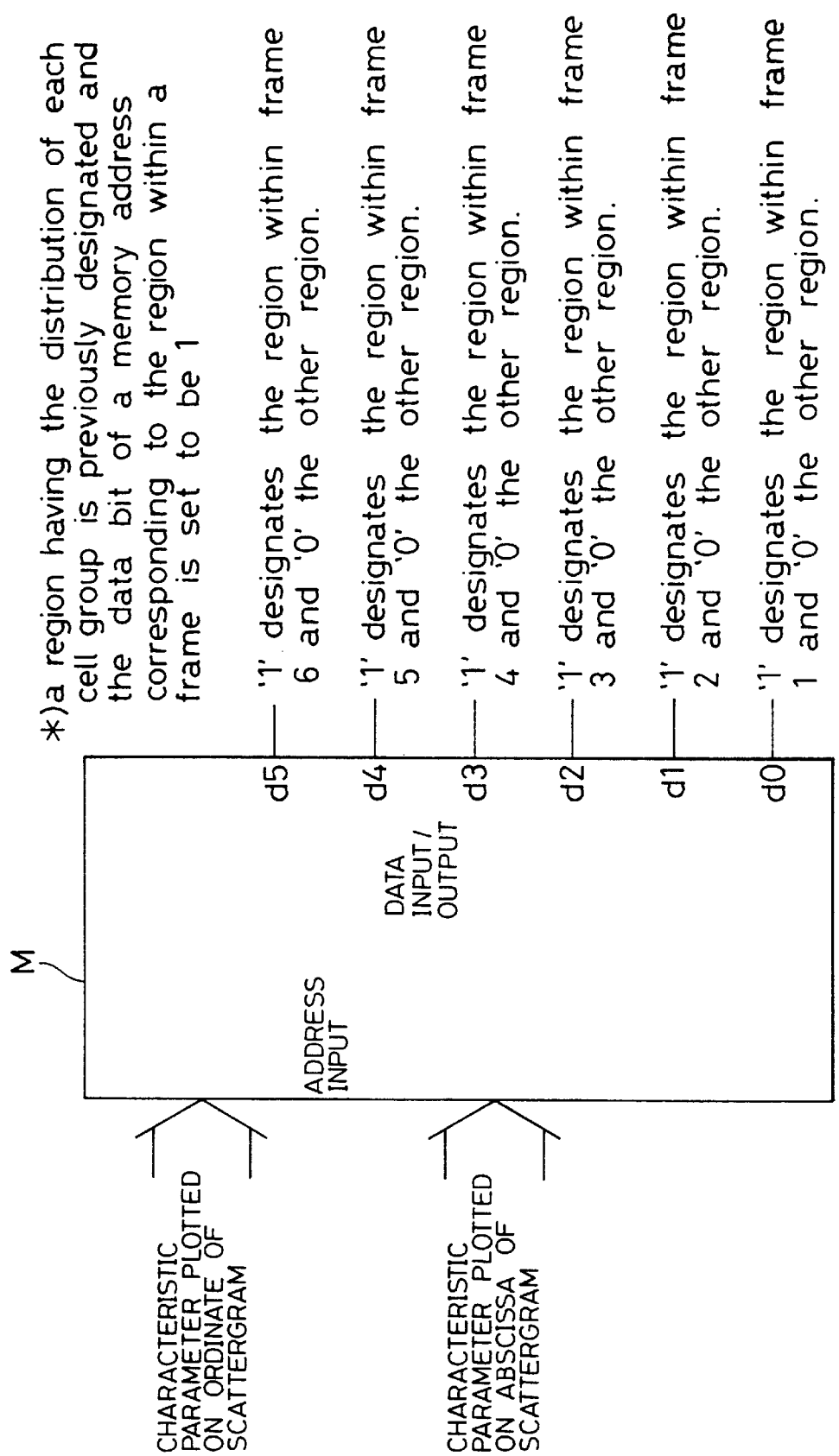
FIG. 8 is an explanatory view for the memory for registering distribution regions in accordance with the present invention.

The imaging control circuit 200 is provided with a memory M for registering distribution regions in which the characteristic parameters of each cell plotted on two axes as the abscissa and ordinate are address-inputted, as shown in FIG. 8, in order to determine whether the values of the characteristic parameters are inside the designated region. The two-dimensional coordinate (scattergram) prepared based on the two characteristic parameters is imaged on memory regions A0, A1 and A2 as shown in FIG. 5. The scattergram is preset so that memory regions (addresses) each corresponding to the region within each frame on the scattergram assume the data bit of 1.

Figure 4:
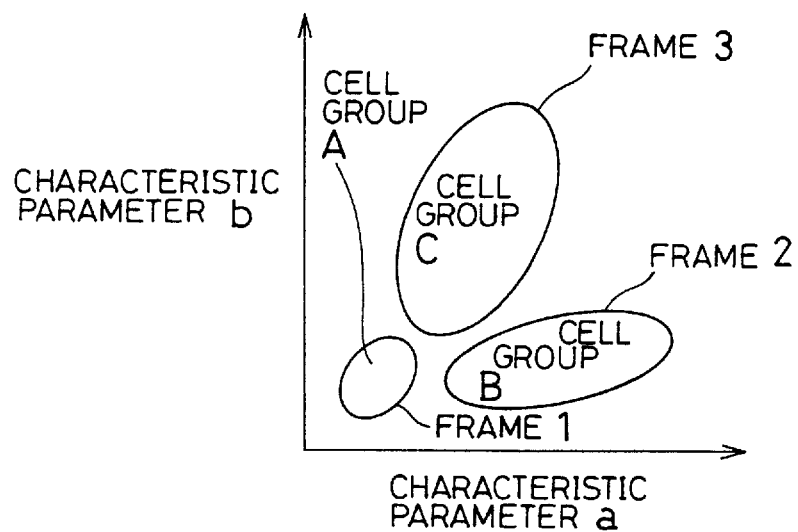
FIG. 4 is an explanatory view for an example of a scattergram in the first embodiment in accordance with the present invention.

In an example shown in FIG. 4, a data bit d0 is allowed to correspond to the frame 1 and the data bit d0 in the memory region corresponding to the frame 1 is set to be 1. In the same manner, the frames 2 and 3 are allowed to correspond to data bits d1 and d2, respectively, and the memory regions corresponding to the frames are set to assume the data bit of 1. In FIG. 5, the memory addresses corresponding to memory spaces in black is set to assume the data bit of 1, whereas the memory address corresponding to regions outside the frames is set to assume the data bit of 0.

Thus, by setting and registering the memory M for registering distribution regions before image capturing, the characteristic parameters of a cell obtained during measurement enables immediate output of the contents of a memory (8 bit data) which assume the values of the characteristic parameters as the memory addresses. Depending on whether each bit of the data is 0 or 1, it is promptly determined which cell group the cells belong to. The memory for registering distribution regions, when the characteristic parameters are 8 bit data for example, has an address space of 8 bits×2=16 bits, i.e., a capacity of 64 k×8 bits.

FIG. 6 illustrates a scattergram in which the characteristic parameters c and d, different from those in FIG. 4, are plotted on two axes as the abscissa and ordinate. In an example of FIG. 6, only the cell group C in the scattergram of FIG. 4 is used to prepare a scattergram with the characteristic parameters c and d in which it is assumed that the distributions of the cell groups C1, C2 and C3 are previously acknowledged to be located within the frames 1, 2 and 3.

This example shows that the cell group C can not be further classified only by the characteristic parameters a and b, but it is classified into three sub-groups by the characteristic parameters c and d. The distribution region of each cell group in the scattergram of FIG. 6 is previously registered in the memory M for registering distribution regions as shown in FIG. 7. During measurement, the characteristic parameters c and d of each cell are inputted in an address line in the memory M for registration.

The imaging control circuit 200, provided with the memory M to previously register the distribution region of each cell group as described above, identifies the kind of each cell in real time by using the characteristic parameters of each cell obtained during measurement. To selectively image a kind of cells, registers R1 and R2 for setting imaging regions as shown in FIGS. 10 and 11 are preset with respect to the kind of cells to be imaged.

Thus, a displayed scattergram is set so as to determine which region is to be selected for imaging cells, by encircling the region in the scattergram. The exemplary register R1 in FIG. 10 can be set so as to determine which frame of which scattergram is selected for imaging cells. Further, it is possible to designate a plurality of frames, thus imaging cells inside the regions obtained by the logic sum (disjunction) or logic product (conjunction) of those frames.

Figure 11:
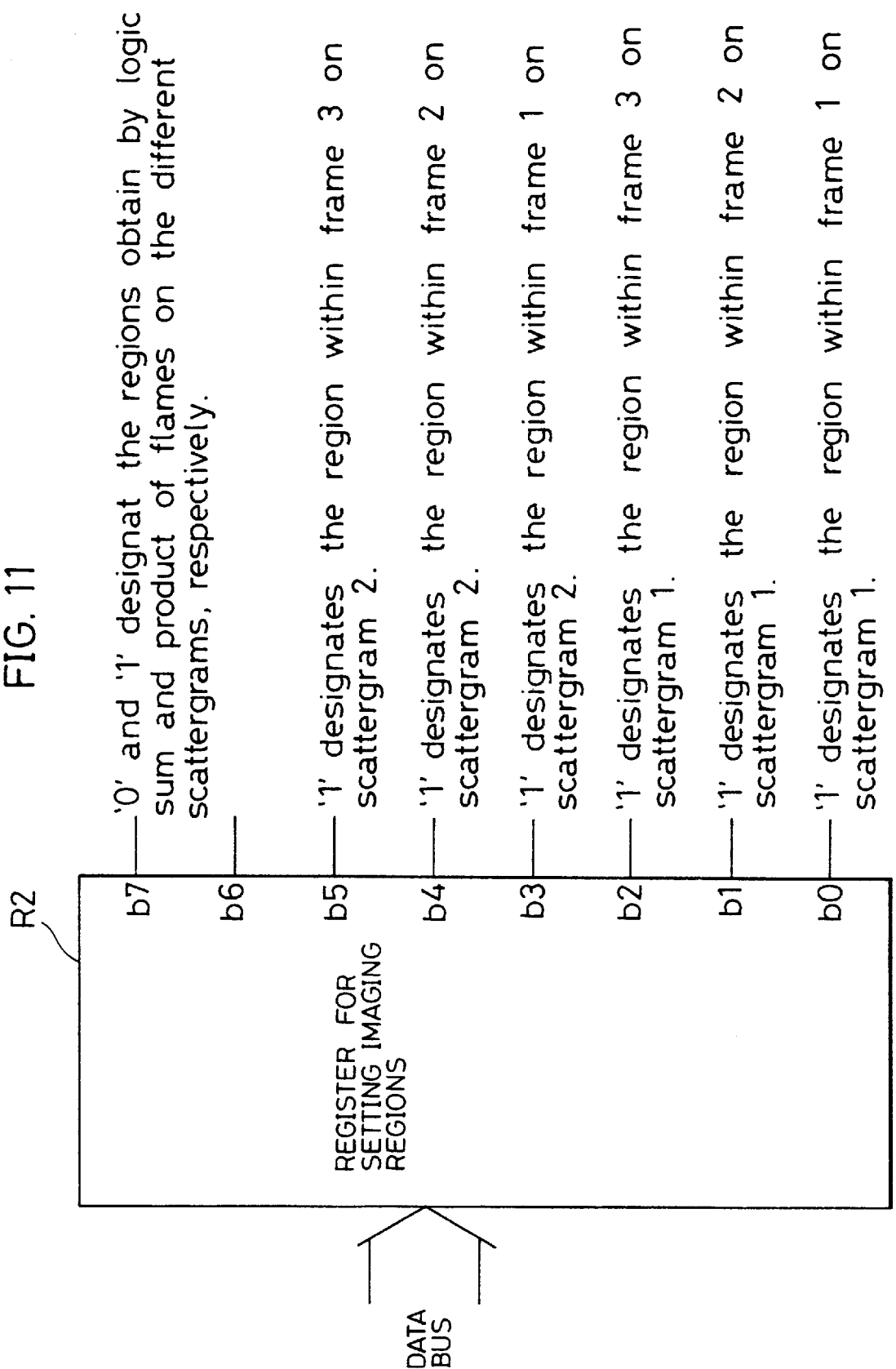
FIG. 11 is an explanatory view for an example of another register for setting imaging regions in accordance with the present invention.

The register R2 for setting imaging regions in FIG. 11 can be set such that each frame in the scattergrams of FIGS. 4 and 6 is designated, thus imaging cells inside the regions obtained by the logic sum or product of those frames in the scattergrams. In FIGS. 4 and 6 for example, the frame 3 in the scattergram of FIG. 4 and the frame 2 in the scattergram in FIG. 6 are designated to obtain the logic product of those scattergrams, thereby selectively imaging cell group C2.

Figure 10:
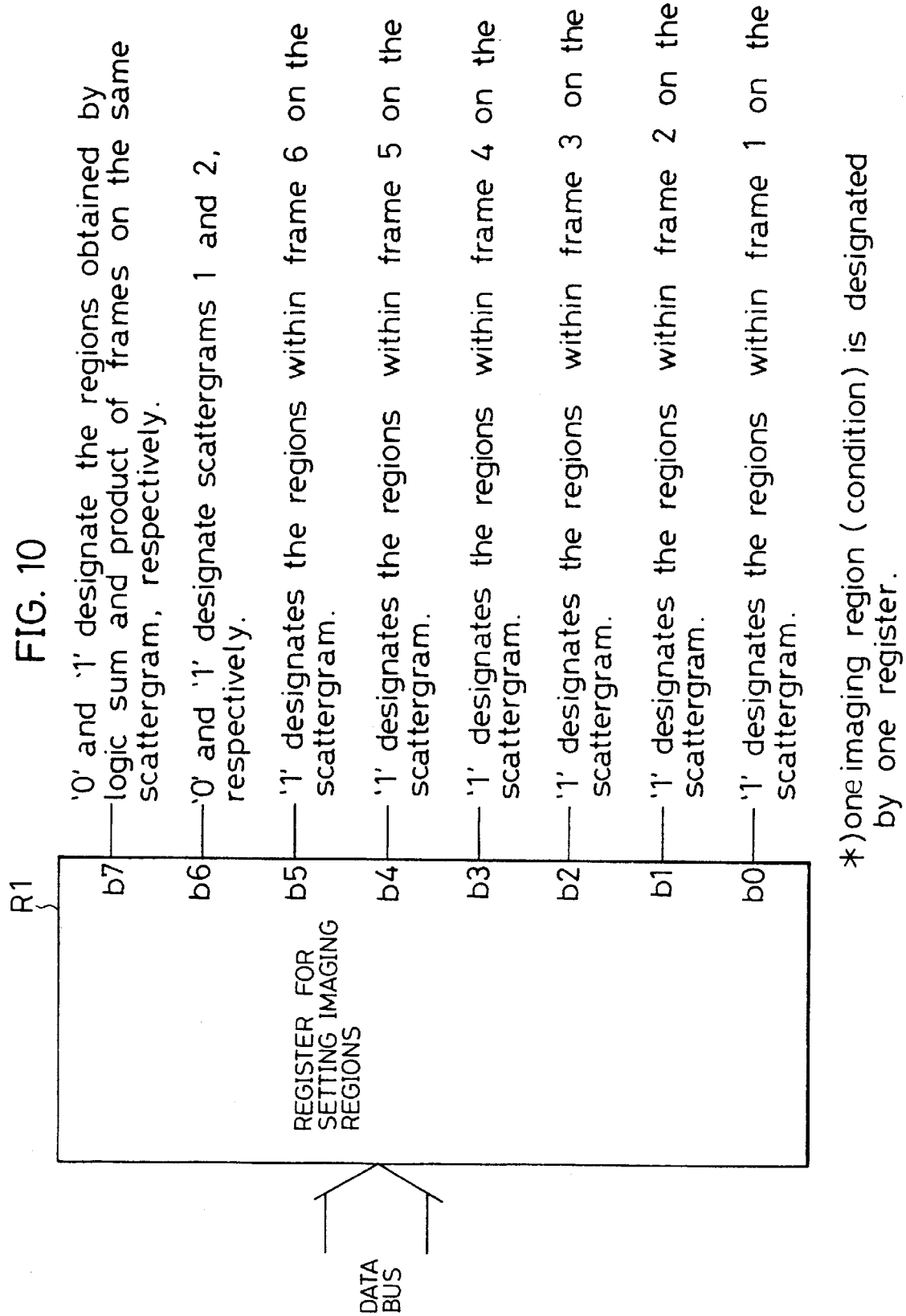
FIG. 10 is an explanatory view for an example of a register for setting imaging regions in accordance with the present invention.

Further, by providing a register for setting the maximum number of captured images in correspondence with the registers R1 and R2 for setting imaging regions as shown in FIGS. 10 and 11, it is possible to make a setting as to what maximum number of captured images is provided during one measurement of cells present inside a region designated by each register for setting imaging regions. Also, by providing plural numbers of each register, it becomes possible to image not only cells of a kind, but also cells of plural kinds by predetermined numbers during one measurement, so that the image memory having a limited capacity can be effectively utilized.

Figure 12:
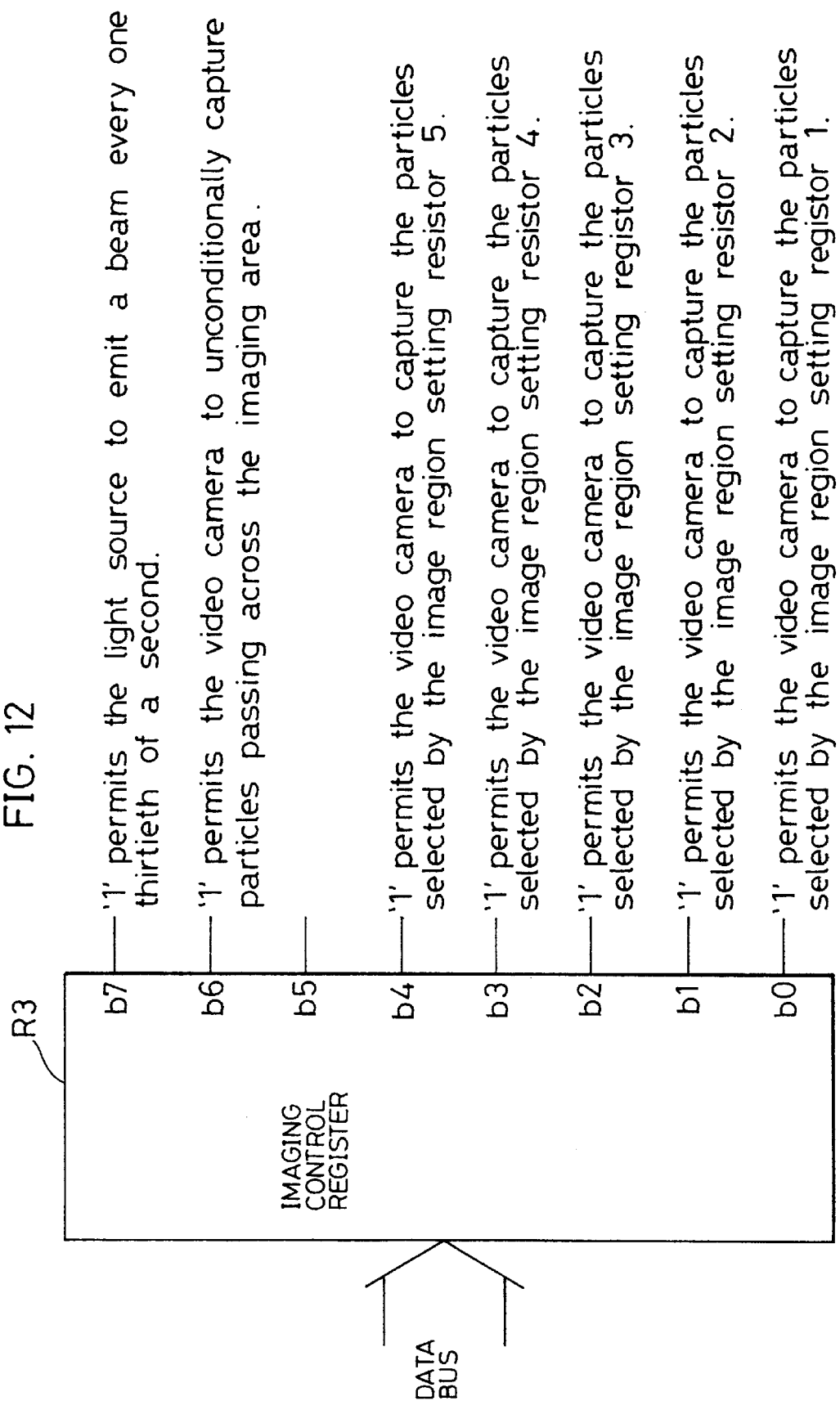
FIG. 12 is an explanatory view for an example of an imaging control register in accordance with the present invention.

Moreover, by providing an imaging control register R3 as shown in FIG. 12, it is possible to actually make a designation so as to determine cells in which region are selectively imaged among the regions set by the plural registers for setting imaging regions, and to facilitate a change in kind or combination of cells to be imaged at each measurement. By setting the bit b6 to be '1', the imaging control register R3 in this example can be set such that any cell is imaged in any condition. By setting the bit b7 to be '1', the pulse light source is allowed to emit light periodically every thirtieth of a second regardless of whether or not cells pass through the sheath flow cell 3. This is convenient in adjusting amount of emitted light, optical axis or the like.

Figure 9:
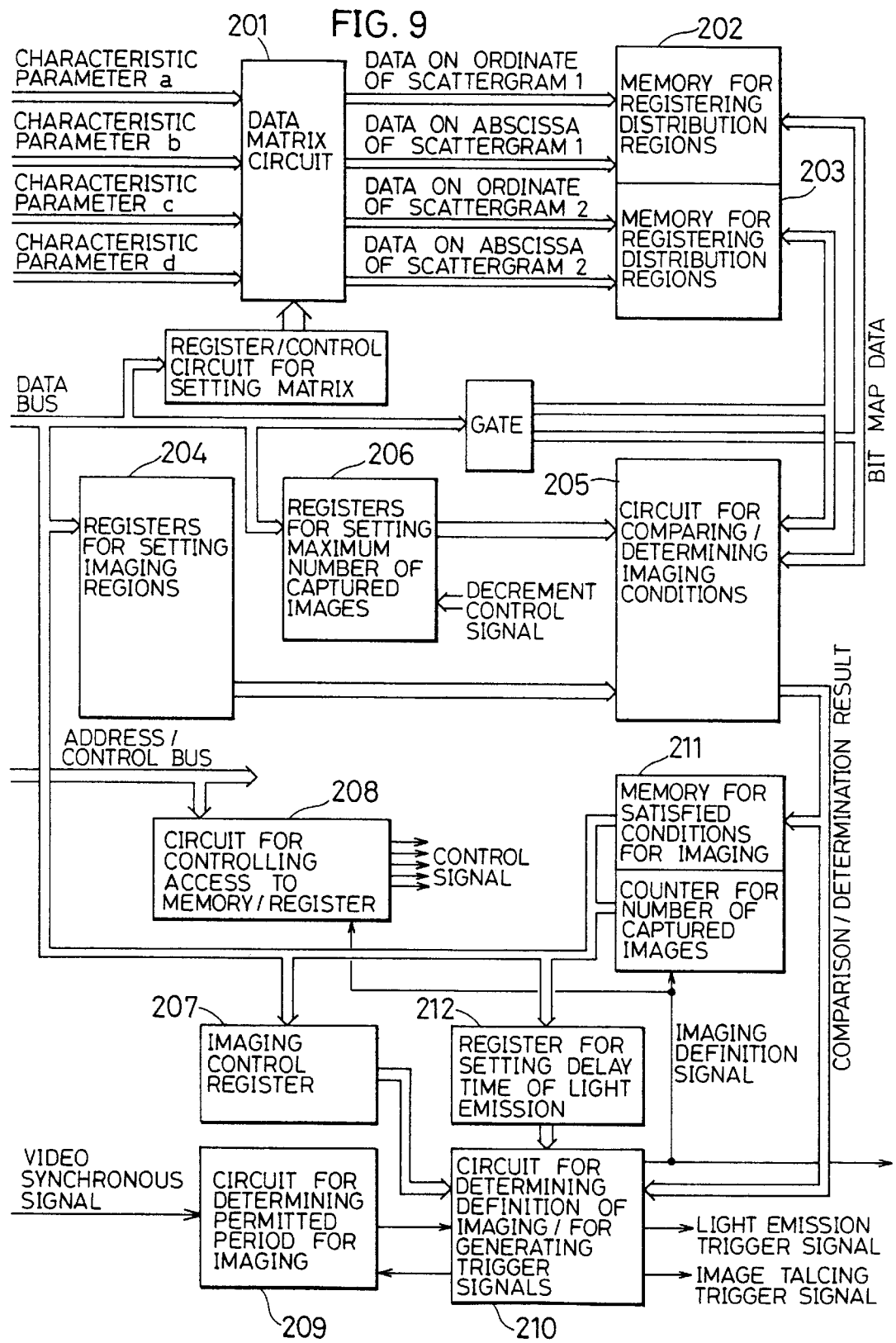
FIG. 9 is a partially detailed block diagram of FIG. 3.

FIG. 9 illustrates a block diagram for an imaging control circuit 200 that realizes the above-mentioned function of imaging control. The characteristic parameters a to d for scattered light and fluorescence intensities obtained in the signal processor 100 are inputted in a data matrix circuit 201. The data matrix circuit 201 has a register for making a setting as to which characteristic parameters the abscissa and ordinate of the scattergrams shown in FIGS. 4 and 6 each are allocated, and the data matrix circuit 201 is preset to have allocation information inputted by the inputting device (not shown). The register for setting allocation enables two characteristic parameters to discretionally be selected and combined to be allocated to the abscissa and ordinate.

Data of the characteristic parameters a and b allocated to the abscissa and ordinate in the scattergram of FIG. 4 are inputted into an address line of a memory 202 for registering distribution regions, and data of the characteristic parameters c and d allocated to be the abscissa and ordinate in the scattergram of FIG. 6 are inputted into an address line of a memory 203 for registering distribution regions. Into the memories 202 and 203 for registering distribution regions are previously written, as shown in FIGS. 5 and 7, map data indicating in which region of a scattergram a cell group of each kind has a distribution.

Registers 204 for setting imaging regions, comprising a plurality of registers as shown in FIGS. 10 and 11, makes a setting as to cells of in which region are imaged among distribution regions registered in the memories 202 and 203 for registering distribution regions. Regions to be imaged are designated in correspondence with bits and the outputs of these registers are connected to a circuit 205 for comparing/determining imaging conditions.

Registers/Counters 206 for setting the maximum number of captured images comprise registers and counters for making a setting and counting as to what maximum number of captured images is provided during one measurement of cells present inside a region designated by each register for setting imaging regions. Each register/counter is coupled with the registers 204 for setting imaging regions. When cells of plural kinds are intended to be imaged during one measurement, the plural registers for setting imaging regions are set for different regions for cells of a kind to be imaged.

The registers/counters 206 for setting the maximum number of captured images are set as to what maximum number of captured images of cells present inside a region designated by each register for setting imaging regions are provided. The counters, which are preset counters each corresponding to each of the registers for setting the maximum number of captured images, are preset before measurement to assume the value of the maximum number of captured image. Each counter is decremented every time cells present inside a region corresponding to the counter are imaged. When the maximum number of captured images is attained, a signal indicative thereof is outputted from the counter to the circuit 205 for comparing/determining imaging conditions.

An imaging control register 207 is adapted to designate which register for setting imaging regions is selected to image the cells present in the region set thereby, as described. By providing the imaging control register 207 as shown in FIG. 12, change in kind or combination of cells to be imaged is facilitated at every measurement.

Setting of the registers and writing into the memories for registering distribution regions as described above are made by the input unit 400 via a data bus before the sample is actually measured and imaged. A circuit 208 for controlling access to memory/register is a circuit for making a control as to which memory/register is set, based on information obtained from the input device.

When the sample is introduced to the sheath flow cell 3 to start measurement and cells reach the irradiation area on which continuous laser beams are applied, the scattered light or fluorescence generated by the cells are detected to provide real time data on signal intensity or signal pulse width (characteristic parameters) of the cells.

These characteristic parameters are inputted in the address line of the memories 202 and 203 for registering distribution regions via the data matrix circuit 201. Map data indicating in which region of a scattergrams cell groups of each kind are distributed are previously written into the memories 202 and 203 for registering distribution regions, as shown in FIGS. 5 and 7. Where the kind of detected cells falls under the cell group B, the bit d1 of 8 bit data outputted from a registration memory 1 (not shown) is made '1' and the other bits are made all '0'. Where the kind of detected cells falls under the cell group C1, the bit d2 of data outputted from the registration memory 1 and the bit d0 of data outputted from a registration memory 2 (not shown) is made '1' and the other bits are made all '0'.

Output data from the memories 202 and 203 are sent to the circuit 205 for comparing/determining imaging conditions. The comparison/determination circuit 205 checks each bit of the output data to momentarily determine whether the data are those for the cells present inside a region designated by the register group 106 for setting imaging regions. Simultaneously, the comparison/ determination circuit 205 checks whether the maximum number of captured images is already attained, and outputs results of comparison/determination corresponding in number to the pairs of the registers 204 for setting imaging regions and the registers 206 for setting the maximum number of captured images, to a circuit 210 for determining definition of imaging/for generating trigger signals.

In imaging cells moving at a high velocity by using a commercially available video camera of the frame accumulation type, it is required to make exposure merely momentarily during an even field period. Even if a number of cells satisfying imaging conditions are detected during the same even field period, exposure and imaging of the cells with the pulse light source are permitted only once. Thus, it is required to provide a circuit 209 for determining permitted period for imaging that determines and controls the period in which cells are permitted to be imaged with the pulse light source. Based on synchronous signals from the video camera 15, the determination circuit 209 checks as to whether it is an even field period, and controls so as not to make exposure by plural times during the same even field period.

In the circuit 201 for determining definition of imaging/ for generating trigger signals, the results of comparison and determination on whether the data satisfy the imaging conditions are compared with information as to which register for setting imaging regions is allowed to offer imaging conditions, i.e., information from the imaging control register. When as a result of the comparison, it is actually determined that the data are those for cells to be imaged, demand signals for imaging are sent to the determination circuit 209, which in turn sends, if it is a permitted time for imaging, permission signals for imaging to the circuit 210 for determining definition of imaging/for generating trigger signals.

Then, the circuit 210 for determining definition of imaging/for generating trigger signal outputs imaging definition signals Ds indicative of definition of imaging to start decrement in a preset counter and increment in an imaging number counter for the satisfied imaging conditions. Simultaneously, information on whether the imaging conditions are satisfied to define imaging is stored in a memory 211 for satisfied conditions for imaging.

Figure 13:
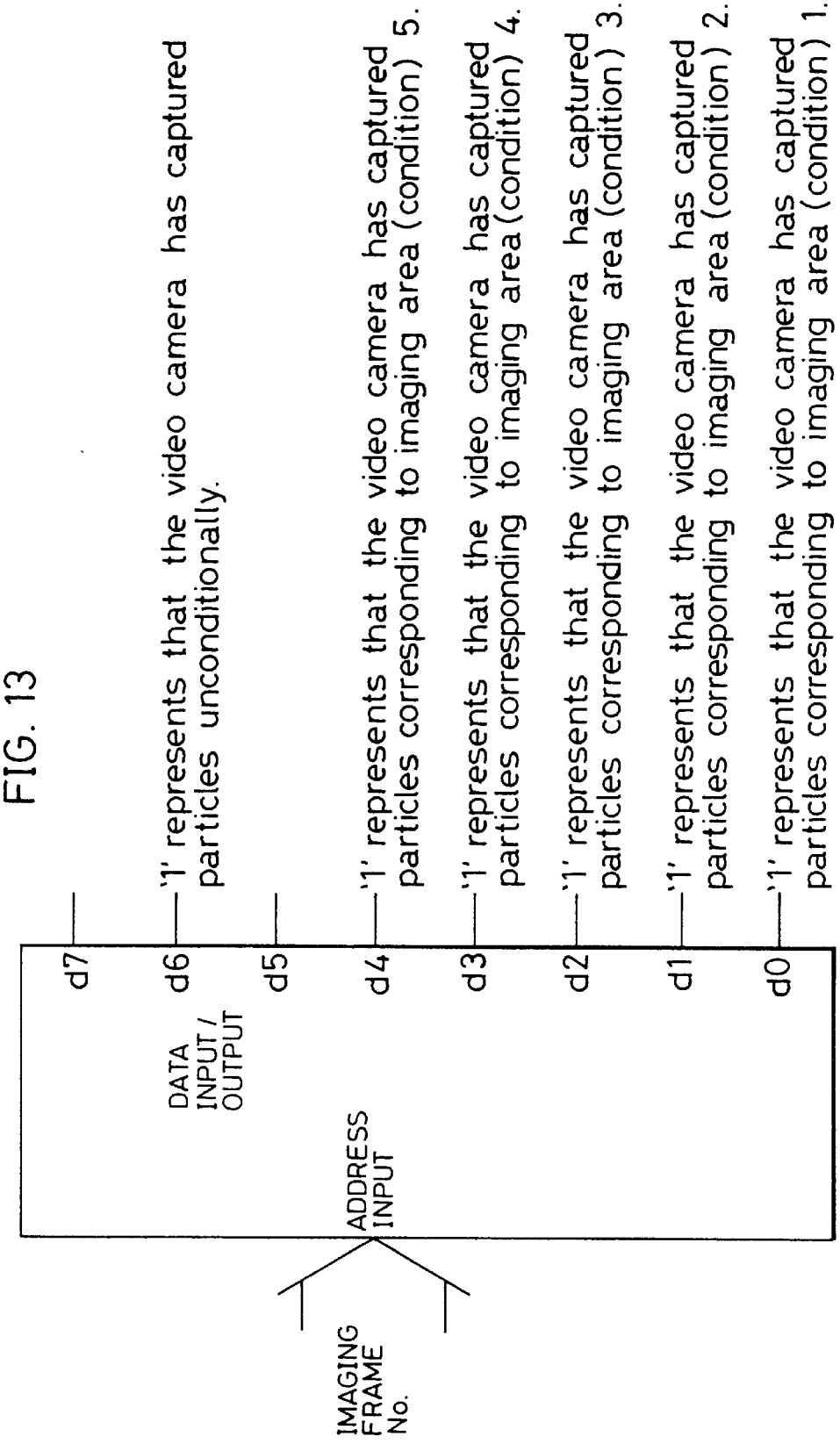
FIG. 13 is an explanatory view for a memory in a satisfied condition for imaging in accordance with the present invention.
Figure 14:
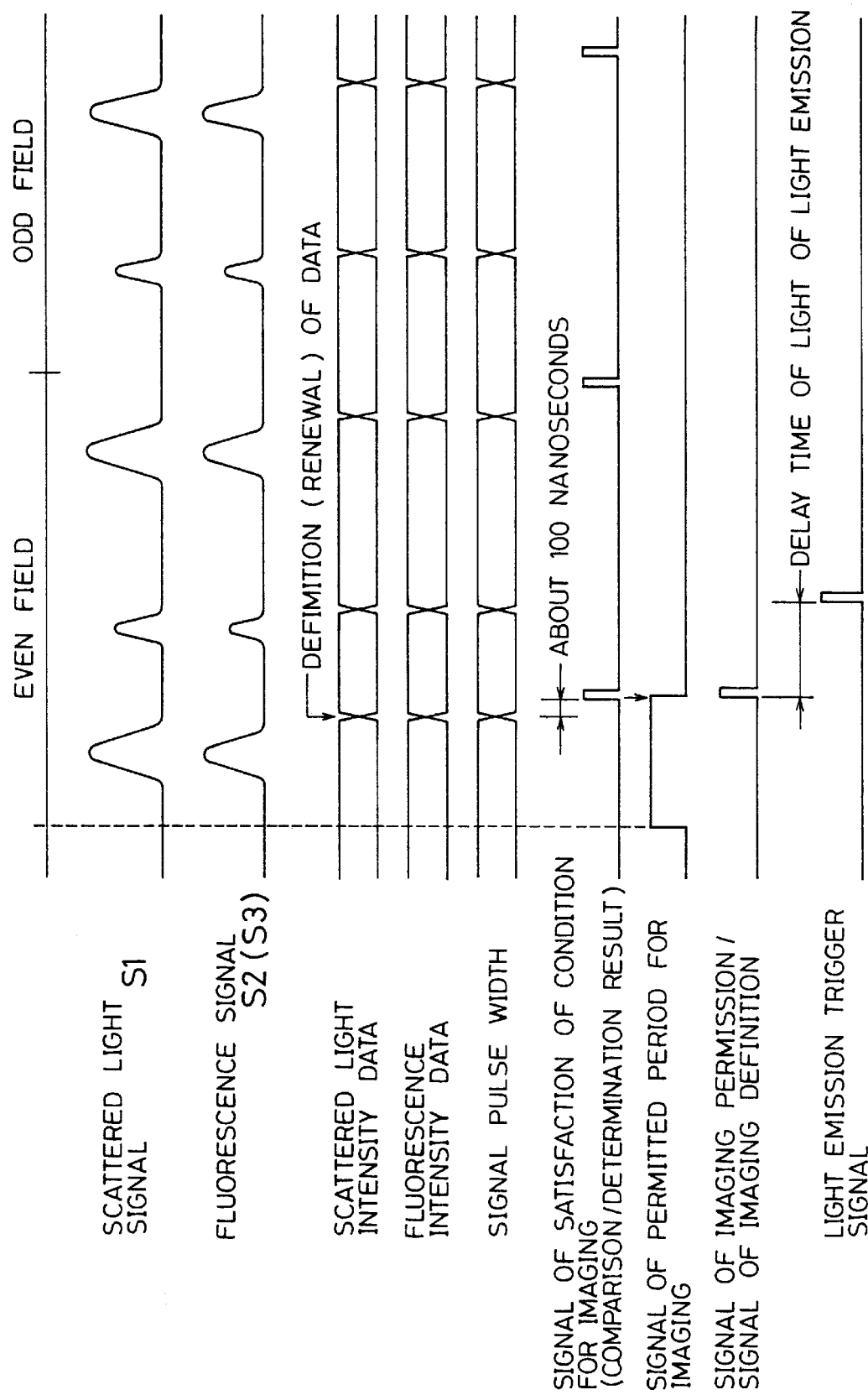
FIG. 14 is a timing chart illustrating an imaging decision processing and an imaging timing in accordance with the present invention.

In the memory 211 for satisfied conditions for imaging as shown in FIG. 13, imaging conditions satisfied by each cell are allowed to correspond to each bit of 8 bit data. Into the address line of the memory 211 is inputted imaging frame numbers for indicating how many times from the start of measurement the imaging is carried out. After the completion of measurement (imagings) of one sample, the satisfied conditions for imaging which are stored in a main memory are read so that the captured and stored images are easily identified in the correspondence to the satisfied conditions.

As shown in FIG. 3, the imaging definition signals Ds are coupled with characteristic parameters for an individual cell and are drawn into the data processor 300. This facilitates the acknowledgement as to cells of which data are actually imaged, and enables selective displaying of points which correspond to the actually imaged cells by giving particular colors or shapes to the points in display.

In the optical system shown in FIG. 1, as described above, the area for imaging cells where pulse light is emitted is located downstream from the area for detecting scattered light or fluorescence generated by the cells. Thus, it is necessary that the pulse light source is allowed to emit light after the lapse of time required for the cells to move to the area where the cells are imaged, after the detection of the scattered light or fluorescence generated by the cells. Supposing the scattered light detection area is shifted by 0.5 mm from the cell imaging area and the velocity of the sample flow is 5 m/second, for example, the pulse light is emitted after the lapse of about 100 nanoseconds from the detection of the scattered light. Thus, it is required to provide a register 212 for setting delay time of light emission as shown in FIG. 9 that presets the delay time of the light emission.

The time required from the detection of the scattered light or fluorescence generated by an individual until the definition of data on its signal intensity and signal pulse width is several nanoseconds or less. About 100 nanoseconds after the definition of the data, comparison/determination results are obtained on whether those data satisfy the imaging conditions. If the data satisfy the imaging conditions, demand signals for imaging are sent to the circuit 209 for determining permitted period for imaging, which in turn immediately sends, if the signals indicate that the data satisfy the imaging conditions during an even field period, permission signals for imaging, to the circuit 210 for determining definition of imaging/for generating trigger signals.

On receipt of the permission signals for imaging, the circuit 210 for determining definition of imaging/for generating trigger signals immediately outputs imaging definition. signal Ds, and simultaneously outputs to the data processor 400 image taking trigger signals It for allowing the image memory 600 to take images. After the lapse of the delay time of about 100 nanoseconds which is set in the register for setting delay time of light emission, the circuit 210 for determining definition of imaging/for generating trigger signals outputs the light emission trigger signals Ts to the pulse light source 2. Images captured by the video camera 15 are taken into the image memory 600 after being analog/ digital converted by the image processor 300, and are displayed in the display device 500 based on conditions inputted from the input unit 400.

In one aspect of the present invention,
1. cells of a kind to be imaged can be arbitrarily designated and imaged substantially without failing to image all the cells of the kind or without erroneously imaging cells of another kind, and
2. designated regions for cells to be imaged can be discretionally combined, even if the designation regions are directed for different purposes for measurement and different kinds of cells to be imaged.

For example, distributions of cells to be imaged are designated by using frames of a shape arbitrarily formed with respect to each of two scattergrams prepared based on different characteristic parameters so as to make it possible to image regions obtained by the logic sum or product of those frames. Thus, any cell group which is not further classified by one scattergram is classified into sub-groups to be imaged when another scattergram is also used for its frames to be combined, thereby giving the logic sum or product of those frames between the scattergrams.

Distribution regions of cells of plural kinds can be simultaneously designated while the maximum number of captured images is preset with respect to cells of designated kinds, so that the image memory with a limited capacity is utilized to image and store cells of plural kinds while simultaneously classifying them during one measurement.

EMBODIMENT 2

A second embodiment of the present invention will now be detailed. The optical system as illustrated in FIGS. 1 and 2 is applied to the second embodiment of the present invention and the explanation thereof is omitted here.

Figure 15:
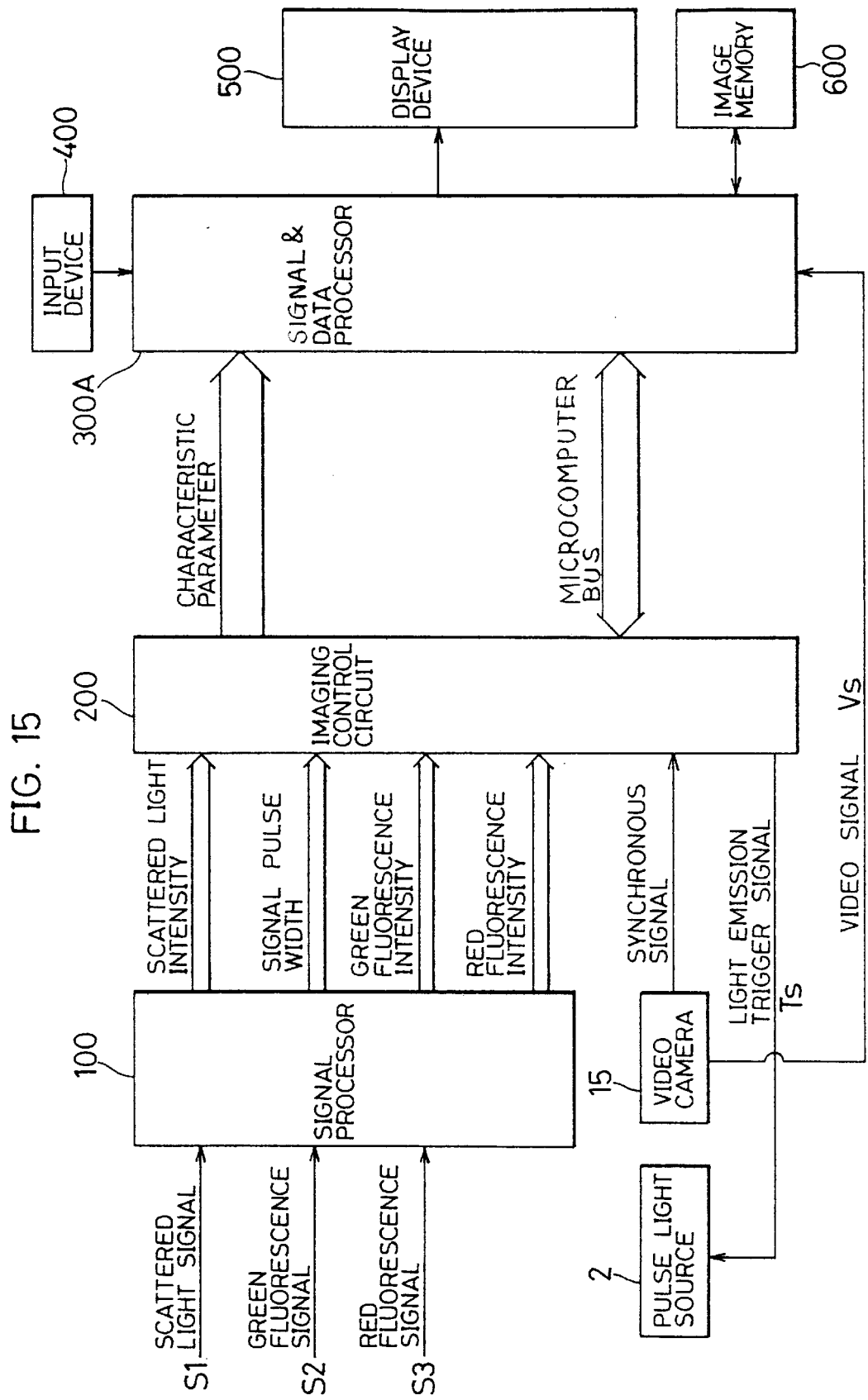
FIG. 15 is a block diagram illustrating the construction of a control system in the second embodiment in accordance with the present invention.

FIG. 15, in which the same elements as in FIG. 3 are denoted by the same reference numerals, illustrates the construction of the signal processing system of the present embodiment. A signal processor 100 provides four characteristic parameters comprising scattered light intensity a, signal pulse width b, green fluorescence intensity c and red fluorescence intensity d. An imaging control circuit 200 identifies the kind of each cell in real time by using those parameters to control so that cells of a kind designated to be imaged are selectively imaged.

In particular, the imaging control circuit 200 compares the characteristic parameters of cells with the characteristic parameters of cells of a targeted kind and supplies, if it is determined that they are the cells to be imaged, light emitting trigger signals Ts for imaging the cells to the pulse light source 2.

The pulse light source 2 is a light source of the type which emits light merely momentarily (for about several nanoseconds) by the light emitting trigger signals Ts, so as to image flowing particles without image blur even at high sample flow velocity of several meters per second. Pulse light, as shown in FIG. 1, is introduced to the flow cell 3 by an optical fiber 12 and is narrowed by a condenser lens 13 to be directed to the sample stream.

The irradiation through the optical fiber 12 reduces coherency of the pulse light, making it possible to capture images of cells with less diffraction fringes. The pulse light transmitted through the sample flow is focused on the photosensing surface of a video camera 15 via a projection lens 14, thereby capturing images of cells formed by the transmitted light. A video signal Vs from the video camera 15 is sent to a data processor 300A as shown in FIG. 15 to be stored and accommodated as a digital image in an image memory 600.

The characteristic parameters a to d for scattered light intensity, fluorescent light intensity or the like are sent to a data processor 300 so as to enable analysis and display for a scattergram (two-dimentional frequency distribution) when those parameters are combined. An input unit 400 including a keyboard and a mouse designates a pair of characteristic parameters for preparing the scattergram, designates regions in the scattergram, and sets the number of image capturing and displaying conditions. Reference numeral 500 represents a display device for displaying scattergrams or images of particles, for example, a CRT. The data processor 100, the imaging control circuit 200 and the data processor 300A are controlled by a micro computer comprising a CPU, a ROM and a RAM.

The operation in this construction will be explained with reference to the flowchart shown in FIG. 16.

Figure 17:
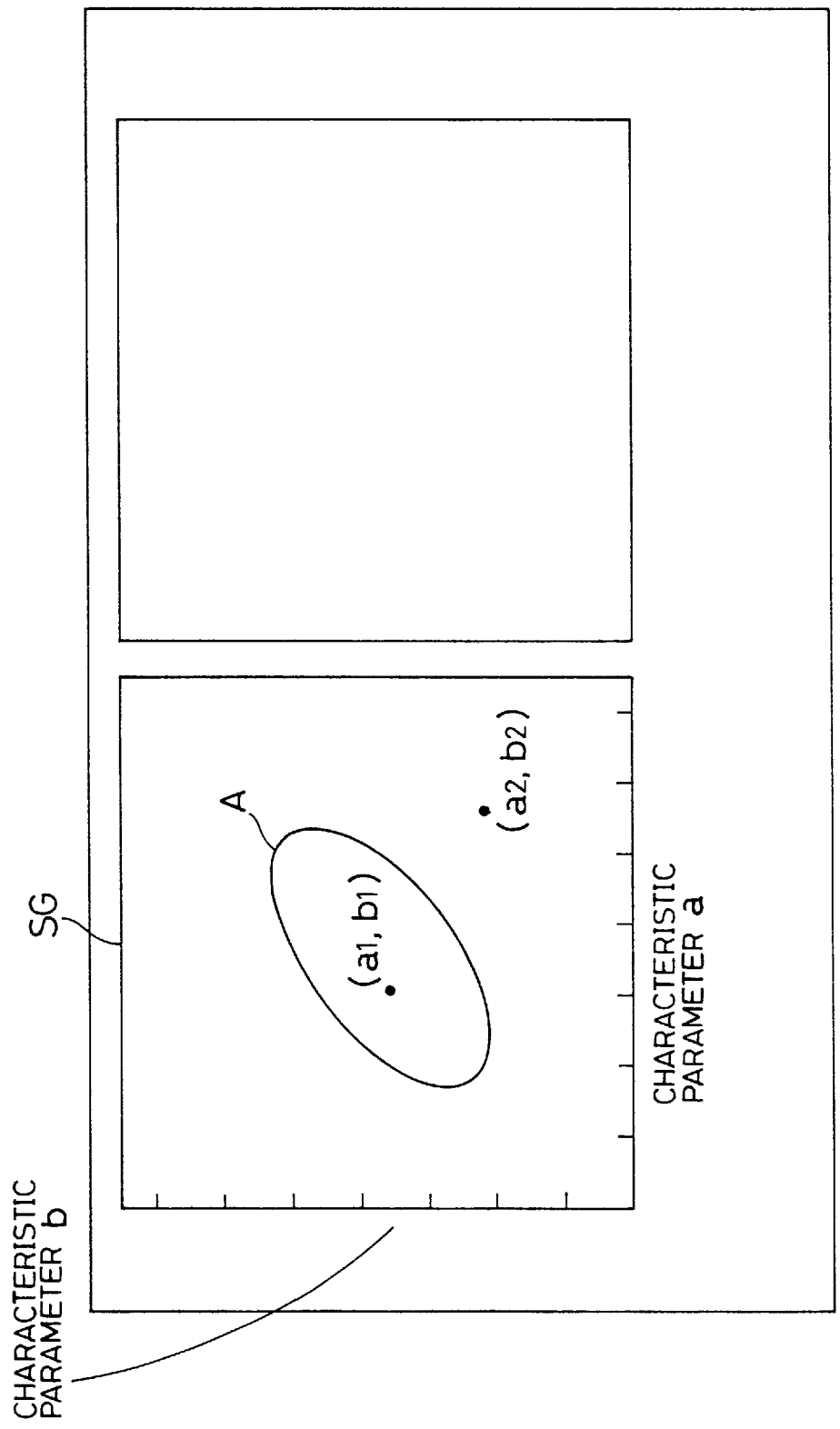
FIG. 17 is an explanatory view for a display example in the second embodiment in accordance with the present invention.

Characteristic parameters a and b designated by a user to be respectively allocated on two axes of the abscissa and ordinate of a scattergram are displayed in a scattergram SG by a display device 500 as shown in FIG. 17. Then, a desired coordinate region A designated by the user by the input device 400 is displayed in the scattergram SG as shown in FIG. 17 (steps S1 and S2).

Cells P1, P2, P3 . . . Pn sequentially flow in the sample stream through the sheath flow cell 3 as shown in FIGS. 1 and 2 and a photodiode 7 and photomultiplier tubes 10 and 11 detect light generated by the cell P1 (step S3). Detection signals S1 to S3 are A/D converted in the signal processor 100 and characteristic parameters a1 to d1 are calculated (steps S4 and S5).

Whether or not the coordinate point (a1, b1) of the cell P1 is located inside the region A is determined (Step S6). If the coordinate point (a1, b1) is located inside the region A as shown in FIG. 17, it is determined by the imaging control circuit 200 whether or not the cell P1 is able to be imaged by the video camera 15 (step S7).

If the cell P1 is determined to be able to be imaged, the imaging control circuit 200 outputs light emission trigger signals Ts to allow the pulse light source 2 to emit light so that the cell P1 is imaged by the video camera 15 (step S8).

Data (8 bit) indicative of the characteristic parameters a, b, c and d which are prepared at step S5 are stored as a data set in memories of the data processor 300 in the order of detection. After imaging of the cell P1 is completed at step S8, the flag bit at the end of the data of the cell P1 is made '1' (ON) and it is recorded that the cell P1 is already imaged (step S9).

With respect to the cell P2 subsequent to the cell P1, the same procedures at the steps S3 to S5 are performed. If the coordinate point (a2, b2) of the characteristic parameters of the cell P2 is determined to be located outside the region A at step S6 as shown in FIG. 17, or if the cell P2 is determined to be unable to be imaged at step S7, the flag bit at the end of the data of the cell P2 is made 0 (OFF) as shown in FIG. 20 and it is recorded that the cell P1 was not imaged (step S10).

Also with respect to the cells P3 to Pn, the same procedures are performed to prepare a data set for the characteristic parameters of the cells P1 to Pn as shown in FIG. 20 (step S11).

Figure 18:
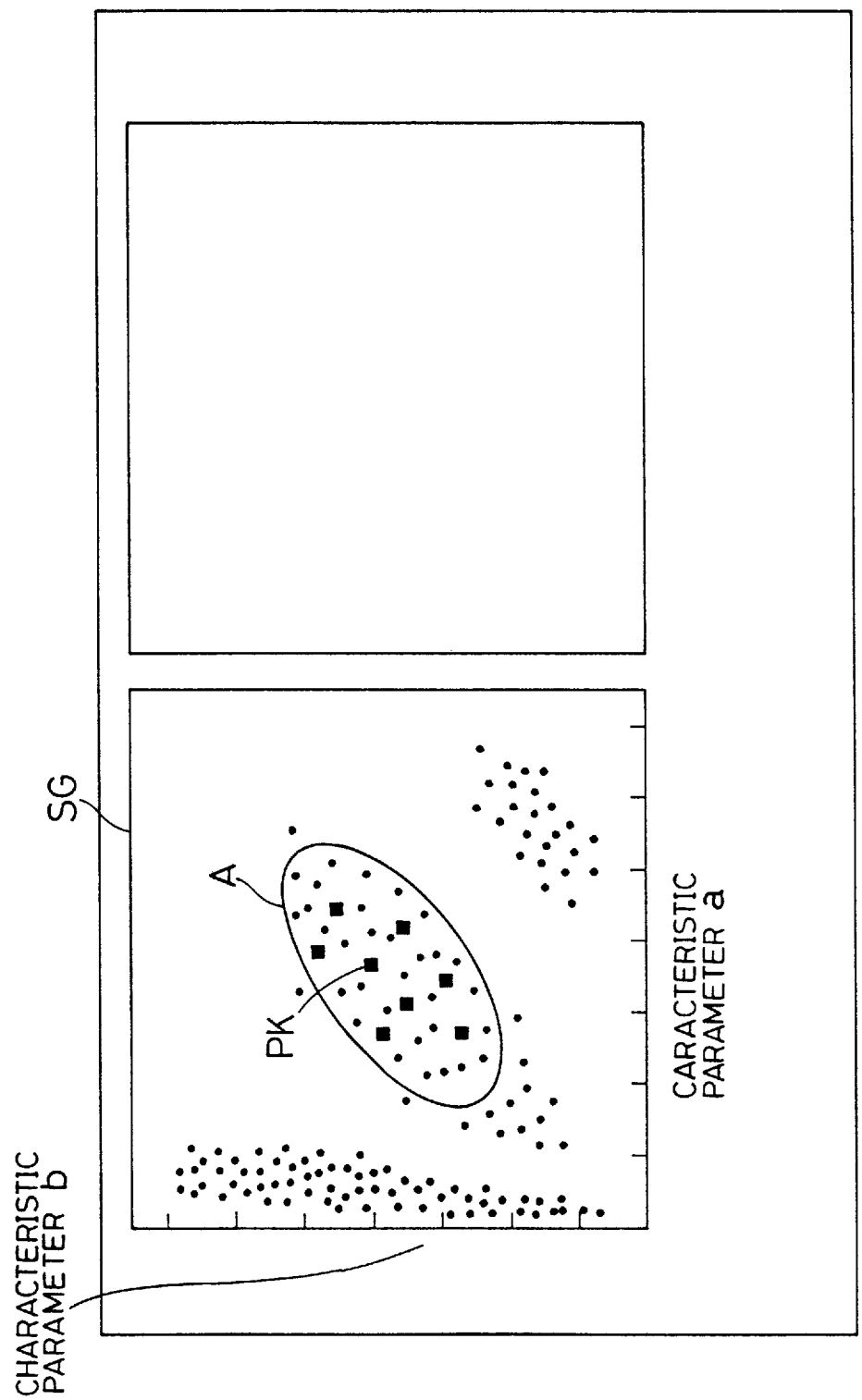
FIG. 18 is an explanatory view for another display example in the second embodiment in accordance with the present invention.
Figure 19:
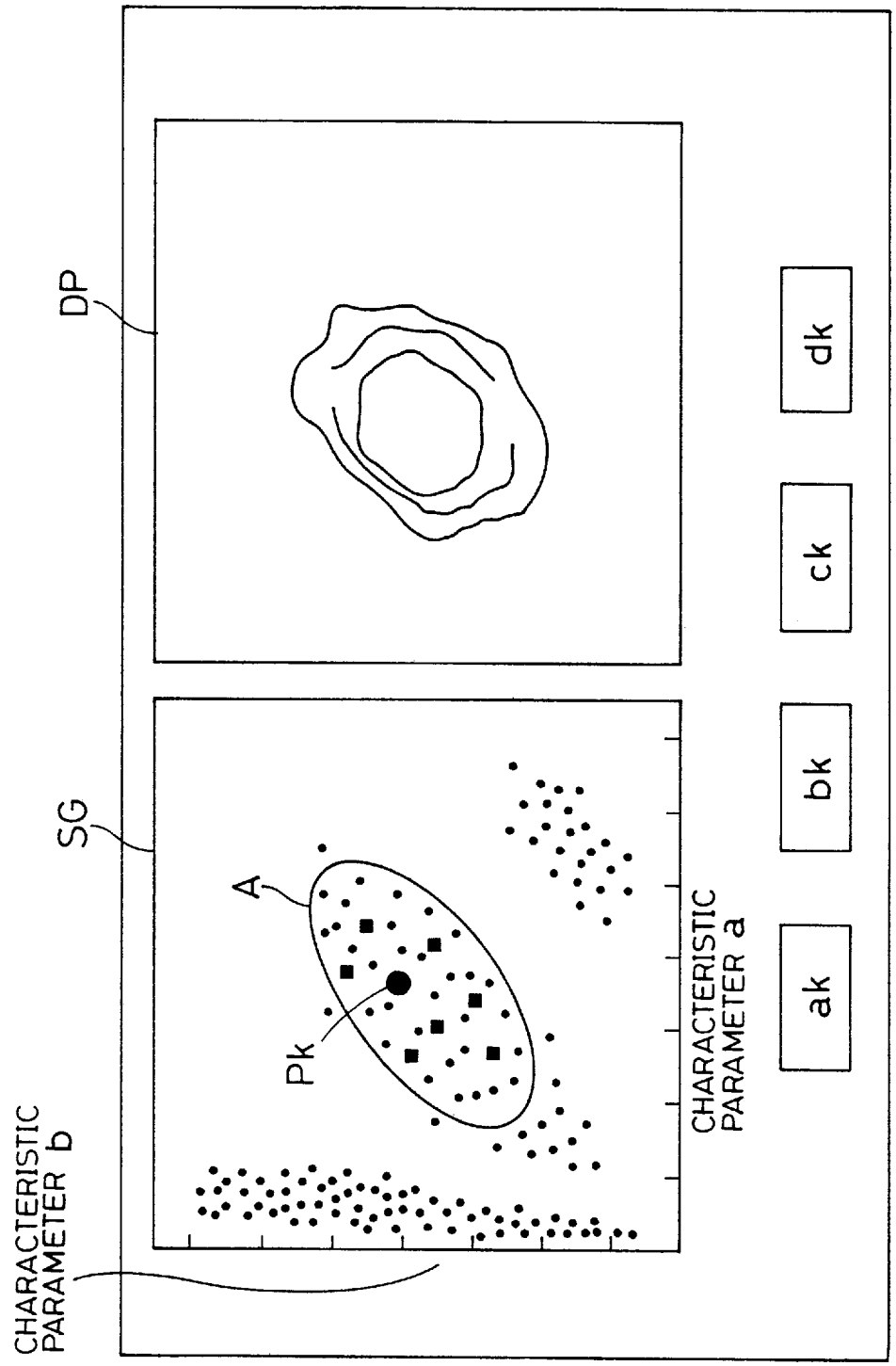
FIG. 19 is an explanatory view for still another display example in the second embodiment in accordance with the present invention.

Each flag bit of the cells P1 to Pn as shown in FIG. 20 is retrieved (step S12) and the coordinate point corresponding to the cells of which the flag bits are 1 is displayed in the scattergram SG to form a black square dot (a first identifier) as shown in FIG. 18 whereas the coordinate point corresponding to cells of which the flag bits are 0 is displayed in the scattergram SG to form a smaller round dot as shown in FIG. 18 (step S14).

When the user designates with the input device 400 the coordinate point corresponding to a cell Pk shown in FIG. 18 among the coordinates displayed in the form of the black square dots (step S15), the dot denoting the coordinate point corresponding to the cell Pk in the scattergram SG is transformed into a larger rounded dot in black (a second identifier) (step S16). Simultaneously, a captured image of the cell Pk is read from memories of the image memory 600 to be displayed onto a display screen DP of the display device 500 (step S17).

At this time, the display device 500 displays the values of the characteristic parameters ak to dk of the cell Pk.

Incidentally, in this embodiment, each coordinate point in the scattergram are represented in the form of a black square dot whereas the coordinate point corresponding to a cell of which the captured image is under display is represented in the form of a larger black dot for the convenience to users, but other shapes and colors of a dot is possible.

In another aspect of the present invention, characteristic parameters and images are stored in correspondence with particles (cells) to be displayed, so that the distribution of the particles is allowed to clearly correspond to captured images of the particles, making it possible for users to observe the shapes of the particles. Further, the present invention is advantageous in that the captured images of the particle can be immediately displayed every time the coordinate point corresponding to a particle is designated in a scattergram. Imaged particles, for example, which are distributed in a region where ordinary cells are absent can be read and displayed. This is of a great help in detecting of abnormal particles. For particles which is unable to be classified only with data of characteristic parameters, they are more accurately analyzed by the users who observe their captured images. Also, captured images of particles are easily utilized as evidence for results of particle classification.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. The flow cytometer in combination comprising:

a sheath flow cell for forming a sample stream containing particles;

detection means for detecting a particle at a first area of the sample stream to generate a signal representative of the particle;

imaging means operatively connected to the detection means for imaging the particle at a second area of the sample stream, the second area being a different area than the first area;

display means for displaying a read image of the particle;

calculation means for calculating a plurality of characteristic parameters indicating characteristics of the particle based on the generated signal;

distribution preparation means for preparing a distribution of the characteristic parameters and displaying the distribution on the display means;

region designation means for designating at least one predetermined region in the distribution;

region storage means for storing the at least one designated predetermined region;

decision means for deciding whether the characteristic parameters of the particle detected at the first area by the detection means are located in the at least one designated predetermined region stored in the region storage means;

imaging control means for allowing the imaging means to image the particle when the characteristic parameters are located in the at least one designated predetermined region;

image storage means for storing the image of the particle obtained by the imaging means; and displaying control means for selectively reading the image of the particle to form a read image and for allowing the display means to display the read image.

2. The flow cytometer of claim 1, wherein the distribution preparation means prepares a plurality of distributions based on the characteristic parameters of the particle designated by parameter designation means and displays the plurality of distributions on the display means, the region designation means designates a predetermined region in each distribution, and the imaging means images the particle when the plurality of characteristic parameters for the particle detected by the detection means are located in the designated regions of the plurality of distributions.

3. The flow cytometer of claim 1, wherein the region designation means designates a plurality of regions in a distribution, and the imaging means images the particle when the plurality of characteristic parameters for the particle detected by the detection means are located in any one of the designated regions of the distribution.

4. The flow cytometer of claim 1, wherein the region storage means stores the at least one designated predetermined region by allowing memory addresses thereof to correspond to the characteristic parameters of the particle so that data bits inside the at least one designated predetermined region and data bits outside the at least one designated predetermined region are represented by different binary data, and the decision means decides whether the characteristic parameters of the particle are located in the at least one designated predetermined region based on the binary data.

5. The flow cytometer of claim 1 further comprising means for presetting the number of imaging times for the imaging means with respect to each predetermined region designated by the region designation means.

6. The flow cytometer of claim 1, wherein the imaging control means comprises triggering signal generating means for generating a signal every time the particle reaches the second area and based on the generated signal, serves to trigger the imaging means.

7. The flow cytometer of claim 1, further comprising coordinate designation means for designating a coordinate point in the distribution, wherein the displaying control means, when the coordinate designation means designates a coordinate point corresponding to the imaged particle, reads the image of the particle corresponding to the designated coordinate point to allow the display means to display the read image of the particle.

8. The flow cytometer of claim 7, wherein the coordinate point corresponding to the imaged particle is represented with a first identifier in the distribution.

9. The flow cytometer of claim 7, wherein the coordinate point corresponding to the the read image of the particle is represented with a second identifier in the distribution.

10. The flow cytometer of claim 1, wherein the detection means includes means for optically detecting the particle.

11. The flow cytometer of claim 10, wherein the imaging means includes a light source.

* * * * *